United States Patent
Pinna et al.

(10) Patent No.: US 6,406,695 B1
(45) Date of Patent: Jun. 18, 2002

(54) TREATMENT OF HEPATITIS C BY ADMINISTRATION OF ANTI-IL-2 RECEPTOR MONOCLONAL ANTIBODY

(75) Inventors: Antonio Pinna; Camillo Ricordi; Andreas G. Tzakis, all of Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 09/429,936

(22) Filed: Oct. 29, 1999

Related U.S. Application Data

(60) Provisional application No. 60/106,266, filed on Oct. 30, 1998.

(51) Int. Cl.⁷ .............................................. A61K 39/395
(52) U.S. Cl. ................................ 424/144.1; 424/143.1; 514/43
(58) Field of Search ........................... 424/143.1, 144.1; 514/43

(56) References Cited

U.S. PATENT DOCUMENTS 5,530,101 A    6/1996   Queen
5,585,089 A    12/1996  Queen

FOREIGN PATENT DOCUMENTS

EP    0 449 769 A    10/1991

OTHER PUBLICATIONS

Utermohlen et al., "T lymphocyte–mediated antiviral immune responses in mice are diminished by treatment with monoclonal antiobdy directed against the interleukin–2 receptor", European Journal of Immunology, vol. 24, No. 12, (Dec. 1994), pp. 3093–3099.

Zervos et al., "Comparison of tacrolimus with microemulsion cyclosporine as primary immunosuppression in hepatitis C patients after liver transplantation", Transplatation, vol. 65, No. 8, (Apr. 27, 1998), pp. 1044–1046.

*Primary Examiner*—Donna C. Wortman
(74) *Attorney, Agent, or Firm*—Pillsbury Winthrop LLP

(57) ABSTRACT

A novel method using anti-interleukin 2 receptor monoclonal antibodies for treating patients having severe viral hepatitis C is described. The inventive method may be used to treat recurrent hepatitis C following liver transplantation, thereby reducing complications in recipients of liver allografts.

1 Claim, No Drawings

TREATMENT OF HEPATITIS C BY ADMINISTRATION OF ANTI-IL-2 RECEPTOR MONOCLONAL ANTIBODY

This application claims the benefit of U.S. Provisional Application No. 60/106,266, filed Oct. 30, 1998.

BACKGROUND OF THE INVENTION

1. Field of the Invention

The invention relates to a new use for existing monoclonal antibodies known to prevent or treat immunological rejection of transplanted organ and tissues. Specifically, the invention provides for the first time a method of using an anti-IL-2 receptor monoclonal antibody for reversing severe viral hepatitis C.

2. Description of Related Art

Recent advances in the field of organ transplantation have lead to the development of new therapy regimens effective in preventing acute rejection episodes in transplant recipients. Several preparations of antibodies are known for use as immunosuppressive agents in treating acute graft rejection. Some of these antibodies interact with certain lymphoid cells, thereby impairing cell function. For example, lymphocyte immune globulin (antithymocyte globulin) can sharply reduce the number of thymus-derived lymphocytes (T-cells) in treated patients and inhibit normal responses of such T-cells. Patients receiving a short course (induction) antithymocyte globulin are typically on other maintenance immunosuppressive regimens (6). The U.S. Food and Drug administration approved in 1998 a commercial form of an anti-interleukin-2 (IL-2) receptor monoclonal antibody for use in kidney transplantation protocols. This anti-IL-2 receptor monoclonal antibody binds to IL-2 receptors to prevent stimulation of T-lymphocyte production in response to a foreign organ graft. T -lymphocytes are major immunological players in the biological mechanisms responsible for organ transplant rejection. Anti-IL-2 receptor monoclonal antibodies, such as basiliximab (Simulect®, Novartis), may be added to current immunosuppressive regimens containing cyclosporine and prednisone for reducing acute rejection episodes in renal transplant recipients. Such regimens appear effective in reducing irreparable damage to allografts subjected to acute rejection, improving post-transplant kidney function.

The addition of basiliximab to current immunosuppressive regimens permits organ recipients to be treated with a two-dose, four-day regimen in lieu of prior five-dose antibody regimens lasting 10 weeks. Basiliximab, cyclosporine and prednisone combination therapies reduce the incidence and severity of acute rejection episodes without increasing rates of infection and other associated consequences of nonspecific immunosuppression.

Similarly, clinical trials of a combination regimen containing daclizumab (Zenapax®, Hoffman-la Roche), mycophenolate mofetil, cyclosporine and corticosteroids have shown such a regimen to be efficacious in reducing acute rejection episodes within six months of kidney transplants. SMART™ Anti-Tac, the humanized monoclonal antibody (daclizumab) active ingredient of Zenapax®, binds to the alpha subunit of high affinity interleukin-2 receptors expressed on activated T-lymphocytes. Daclizumab antagonizes binding of IL-2 to high affinity IL-2 receptors, thereby suppressing T-lymphocyte activity against allografts.

Daclizumab-based therapy regimens improve organ transplant survival without unduly increasing therapy toxicity. Such humanized monoclonal antibodies have a longer half-life and are less likely to be targeting by a patient's immune system than non-humanized antibodies, such as previously tested mouse monoclonal antibodies. Humanized immunoglobulins are disclosed in, for example, U.S. Pat. Nos. 5,530,101 and 5,585,089.

Recurrence of hepatitis C following liver transplantation remains a feared complication in recipients of liver allografts. Frequent recurrence of hepatitis C infection following orthotopic liver transplantation (OLT) is common, affecting up to 75% of transplant recipients (1). Hepatitis C viral RNA is detected in 95% to 100% of liver transplant patients suffering from recurrent hepatitis C. Traditionally, severe hepatitis C recurrence following liver transplantation is treated by reduction or discontinuation of immunosuppressive therapy and a combination of antiviral drugs such as alpha interferon and ribavirin, a regimen which has proven to be ineffective. Severe hepatitis C or cirrhosis secondary to hepatitis C continue to be complicating factors in liver transplantation.

As noted herein, antiviral therapy for recurrent hepatitis C viral infection post-orthotopic liver transplantation has failed miserably to date. Cholestatic hepatitis has an incidence of 8% to 13% with a high morbidity level. Characteristics indicative of cholestatic hepatitis include early hepatitis C virus recurrence, moderate to high bilirubin levels, renal insufficiency, ascites, and elevated serum hepatitis C viral RNA concentrations (3).

Recent experimental evidence suggests that viral specific cytotoxic T-lymphocyte activation could be an important pathogenic mechanism of hepatocellular damage during chronic hepatitis C (2). Other studies indicate that only cells infected with non-cytopathic replicating viruses are destroyed by activated cytotoxic T-lymphocytes, due to viral induced expression of endogenous major histocompatibility complex (MHC) class I molecules (4). Cross-presentations of antigens expressed in virally infected peripheral organs could explain activation of cytotoxic T-lymphocytes (5).

Therefore, a need exists for improved therapy for patients with hepatitis C and against hepatitis C virus recurrence in patients undergoing liver transplantations.

SUMMARY OF THE INVENTION

Treatment of patients with severe hepatitis C by an anti-IL-2 receptor antibody according to the invention may result in selective blockade of the effector cytopathic mechanism of hepatocellular damage, while concurrent anti-viral therapy eventually decreases the viral load in such patients.

An embodiment of the invention is a method of treating viral hepatitis C in a patient comprising combining an effective amount anti-IL-2 receptor monoclonal antibody with an effective amount of at least one antiviral compound for administration to a patient;

administering to a patient a dosage of the combination of anti-IL-2 receptor monoclonal antibody and at least one antiviral compound; and repeating administration of said dosage until liver function tests yield values in a clinically acceptable range, wherein said dosage comprises administering either simultaneously or sequentially the anti-IL-2 receptor monoclonal antibody and the at least one antiviral compound.

Optionally, the method of treating viral hepatitis C in a patient may further comprise pretreating patients with an antihistamine or acetaminophen.

Another embodiment of the invention is a method of treating viral hepatitis C in a patient, wherein the patient is a liver transplant recipient suffering from recurrent cholestatic hepatitis C.

Yet another embodiment of the invention is a method of treating viral hepatitis C in a patient, wherein the effective amount of anti-IL-2 receptor monoclonal antibody comprises a dose of 2 mg/Kg of body weight.

Still another embodiment of the invention is a method of treating viral hepatitis C in a patient, wherein the dosage comprises a combination of an intravenously administered anti-IL-2 receptor antibody and at least one antiviral compound.

A further embodiment of the invention is a method of treating viral hepatitis C in a patient, wherein the dosage is repeated once weekly for up to six weeks.

A further embodiment of the invention is a method of treating viral hepatitis C in a patient, wherein a dosage comprises intravenously administering anti-IL-2 receptor monoclonal antibodies once every other week, and thereafter dosing is repeated monthly for at least one year.

DETAILED DESCRIPTION OF THE INVENTION

Recurrent cholestatic hepatitis C may be treated by reducing or suspending maintenance immunosuppression of patients, and administering anti-IL-2 receptor monoclonal antibody (Daclizumab) as a combination therapy with α-interferon and ribavirin. Doses of α-interferon typically are in the range of several million units. Ribavirin is administered at a level titrated to minimize side effects. Specifically, ribavirin may be administered in daily oral doses of 400 mg twice daily. Concurrently, for example, three million units of α-interferon may be injected subcutaneously three times weekly. In addition, 2 mg/Kg of anti-IL-2 receptor monoclonal antibodies are administered intravenously, initially once per week, a frequency later reduced to once per month.

Patients may undergo an initial induction period, during which time one injection of anti-IL-2 receptor monoclonal antibodies is given every other week for five weeks, and thereafter the injections are repeated monthly for at least one year. The treatment strategy may be individualized depending upon the viral load and biochemical response of each patient.

Other immunosuppressive drugs previously tested proved either to have no effect on hepatitis C, or they undesirably increased or accelerated the progression of the disease. This generally required a decrease or discontinuation of immunosuppressive therapy.

Factors considered in the decision to use an anti-IL-2 receptor monoclonal antibody to block activated cytotoxic T cells against infected hepatocytes include: the clinical conditions of the patients; the histology of a prior hepatic biopsy; and preliminary results of another study in which high dose donor bone marrow infusions significantly reduced the recurrence of hepatitis C. Selective blockade of activated T cells by the anti-IL-2 receptor monoclonal antibody daclizumab halted the progress of severe hepatic damage by hepatitis C, while allowing for other immune components to maintain antiviral activity. This antibody therapy was clinically successful in patients, establishing the potential life-saving role of the inventive treatment in severe cases of hepatitis C.

Typically, the dosage of anti-IL-2-receptor antibody is similar or identical to dosages recommended by the FDA. Monitoring IL-2 receptor titer and the HCV-RNA viral load can be helpful in titrating the dosage of anti-IL-2 receptor antibody and the length of treatment. The anti-IL-2-receptor antibodies are given to a patient by an intravenous route, either concurrently or sequentially, with the combined antiviral treatment comprising subcutaneous (s.c) administration of α-interferon and oral (po) administration ribavirin. Preferred diluents or pharmaceutical carriers were those suggested by the pharmaceutical manufacturer of the α-interferon. Preferably, patients are pretreated with an antihistamine or acetaminophen in order to alleviate the well-known side effects of α-interferon. The treatment may initially comprise 5 dosages administered within a week, every other week, and thereafter repeating dosing monthly for at least one year. This new use for anti-IL-2receptor antibodies may be extended to patients with hepatitis C before a liver transplant becomes necessary, as well as to patients following liver transplantation to prevent recurrence of the disease.

Following confirmation of these pilot trials, anti-IL-2 monoclonal antibodies will be further tested in treating autoimmune diseases, including type 1 diabetes, multiple sclerosis, lupus, Crohn's disease, and the like. Heretofore, anti-IL-2 receptor antibodies have never been used for any of the above-described new applications. In patients with a primary autoimmune disease or with recurrent autoimmune disease after transplantation, a course of high dose intravenous anti-IL-2 receptor monoclonal antibody (2 mg/Kg) may be instituted, to block the effector cells (cytotoxic T cells expressing the IL-2 receptor) until the clinical, biochemical and pathology expression of the autoimmune disorder disappear.

Blockade of the autoimmune response may enable preservation of the target cells, while therapeutic strategies are implemented to eliminate the underlying autoimmunity that could eventually be responsible for recurrence of the disease. Some of these strategies currently under investigation include bone marrow/stem cell transplantation as well as treatment with monoclonal antibodies, such as non depleting anti CD3 antibodies and/or antibodies directed at blockade of co-stimulatory pathways (e.g., anti CD154, anti-B7) or anti CD45RB. The invention is further illustrated by the following non-limiting examples.

EXAMPLES

Example I

Three male patients, ages 54, 54 and 53, underwent orthotopic liver transplantation for end stage liver disease secondary to hepatitis C. Immunosuppression after transplant consisted of Tacrolimus (Prograf, Fujisawa) and glucocorticoids. All three patients developed recurrent hepatitis C within 60 days of receiving transplanted livers. Diagnosis of hepatitis C was made by liver biopsy, elevated liver function test and determination of hepatitis C RNA viral load levels using a commercially available kit (Chiron Corporation, Emeryville, Calif.). Therapy was initiated in each patient at the time of recurrence comprising α-interferon at a dose of 3 million units s.c. three times a week+ribavirin 400 mg po twice a day. Concurrently, immunosuppression was decreased by reducing the administered doses of Tacrolimus to only 1 mg po a day and the steroidal therapy was stopped. None of the patients so treated responded to this therapy after an average of 1 month.

Additional liver biopsies confirmed recurrent hepatitis C, with moderate to severe activity and elevated hepatitis C RNA serum levels (>120×$10^6$ Eq/ml, 31.7×$10^6$ Eq/ml and >120×$10^6$ Eq/ml). Intravenous daclizumab at a dosage of 2 mg/Kg body weight once a week was started, while all remaining maintenance immunosuppression comprising Tacrolimus and steroids was ceased. Antiviral therapy remained unchanged. Daclizumab treatment continued weekly for five doses averaging 4 to 6 weeks in length until a decrease of the patient's bilirubin levels was observed, together with improvement of the histological markers of recurrent hepatitis C at the liver biopsy and clinical improvement of the patients. At that point, HCV-RNA viral load of the patients was significantly reduced or undetectable, despite being persistently high before the anti-IL2-receptor antibody treatment was started.

A remarkable clinical improvement was observed in all three patients between two and four weeks from the onset of daclizumab treatment. At the same time, only mild to minimal hepatitis was detected in follow-up liver biopsies. Significant decreases in direct bilirubin levels were measured in two of the three patients (from 30 to 10 mg/dL in one and from 5 to 0.5 mg/dL in the other) after three weeks of daclizumab therapy. Hepatitis C viral RNA levels decreased from >120×10$^6$, 31.7×10$^6$ and >120×10$^6$ Eq/ml to 2.2×10$^6$ Eq/ml, 7.6×10$^6$ Eq/ml and non-detectable levels, respectively. Two of the treated patients were discharged and are currently well at home, while the third was able to resume normal activity after two weeks of antibody treatment according to the invention.

Example II

The above-described daclizumab regimen was carried out on a total of 11 patients with recurrent cholestatic hepatitis C, each of whom had previously received α-interferon plus ribavirin combination therapy. The mortality for recurrent cholestatic hepatitis C is typically about 90%. Of the 11 patients receiving the inventive therapy of 2 mg/kg body weight intravenous daclixumab once weekly for 4 to 6 weeks, in combination with antiviral agents, only one patient failed to survive. That patient died three months after treatment with Zenapax due to causes unrelated to the treatment (aspiration pneumonia). Three patients underwent liver retransplantation for either chronic rejection (2 patients) or untreatable cholestatic hepatitis C (1 patient).

Table 1 shows the modification of the liver pathology after treatment, the evolution of the clinical picture of the 11 patients and the viral RNA HCV load obtained before and after the antiviral/anti-IL-2 receptor monoclonal antibody regimen.

Use of the inventive method in these patients having severe recurrent hepatitis C after liver transplantation resulted in dramatic improvement in liver function tests (bilirubin, AST, ALT), clinical conditions and renal function. Typically, hyperbilirubinemia occurs at blood levels of bilirubin greater than about 1.0 mg/dL. Severe hemolytic anemia usually does not produce sustained elevation of blood bilirubin levels greater than about 4.0 mg/dL, unless hepatic bilirubin clearance is compromised. However, patients experiencing liver dysfunction, such as those suffering from viral hepatitis in combination with a hemolytic disease, may have circulating levels of bilirubin approaching 100 mg/dL. The figures in Table 1 show the overall ability of the inventive therapy to reduce bilirubin levels in patients with hepatitis C to a clinically acceptable range. Prior to treatment, these patients were in critical condition, but resumed nearly normal lives following therapy according to the invention.

Thus, results indicate that anti-IL-2 monoclonal antibodies are effective for controlling cholestatic hepatitis C in patients following liver transplantation, as well as for controlling hepatitis C in patients before liver transplantation becomes necessary.

The foregoing description of the invention has been provided for the purposes of illustration. It is not intended to be exhaustive or to limit the invention to the precise embodiment(s) disclosed. The embodiment(s) were chosen and described in order to best explain the principles of the invention and its practical application, thereby enabling others skilled in the art to understand the invention for various embodiments and with various modifications as are suited to the particular use contemplated.

All journal articles, books, patents and publications cited herein are hereby incorporated in their entirety herein by reference.

REFERENCES

1. Ascher N L, Lake, J R, Emond J, Roberts J. Liver Transplantation for Hepatitis C Virus-Related Cirrhosis. *Hepatology* 1994; 20: 245–275.
2. Asanza C G, Garcia-Monzon C, Clemente G, Salcedo M, Garcia-Buey L, Garcia-Iglesias C, Banares R, Alvarez E, Montero-otero R. Immunohistochemical Evidence of Immunopathogenic Mechanisms in Chronic Hepatitis C Recurrence After Liver Transplantation. *Hepatology* 1997; 26(3): 755–763.

TABLE 1

| | Bilirubin, HCV titer and liver biopsy before treatment with Zenapax | | | Bilirubin, HCV titer and liver biopsy after treatment with Zenapax | | | Outcome | |
| --- | --- | --- | --- | --- | --- | --- | --- | --- |
| Name | Bil | HCV | Liver Biopsy | Bil | HCV | Liver Biopsy | Re-transplant | Status |
| Dea | 25 | 120,000,000 | Cholest.HCV | 3 | 250,000 | | no | dead |
| Lam | 20 | 100,000,000 | Cholest.HCV | 20 | 200,000 | chr.rej. | yes | alive |
| Ass | 10 | 120,000,000 | Cholest.HCV | 0.8 | 200,000 | normal | no | alive |
| Gar | 5 | 15,000,000 | Cholest.HCV | 0.8 | 600,000 | normal | no | alive |
| Rob | 5 | 120,000,000 | Cholest.HCV | 0.7 | 200,000 | chr.hcv | no | alive |
| Sho | 18 | 84,400,000 | Cholest.HCV | 1 | 5,000,000 | chr.hcv | yes | alive |
| Edw | 10.5 | 120,000,000 | Cholest.HCV | 0.5 | 49,000,000 | normal | no | alive |
| Joh | 14 | 110,000,000 | Cholest.HCV | 4 | 8,300,000 | chr.hcv | no | alive |
| Smi | 20 | 120,000,000 | Cholest.HCV | 20 | 3,700,000 | chr.rej. | yes | alive |
| Gra | 5 | 120,000,000 | Cholest.HCV | 1.3 | 26,800,000 | | no | alive |
| Ian | 4 | 120,000,000 | Cholest.HCV | 1 | 8,300,000 | | no | alive |

3. Schluger L K, Sheiner P A, Thung S N, Lau J Y N, Min A, Wolf D C, Fiel I, Zhang D, Gerber M A, Miller C M, Bodenheimer H C. Severe Recurrent Cholestatic Hepatitis C Following Orthotopic Liver Transplantation. *Hepatology* 1996; 23:971–976.
4. Zinkernagel R M, Doherty P C. The Discovery of M H C Restriction. *Immunology Today* 1997; 18:14–17.
5. Carbone R F, Kurts C, Bennett S R M, Miller J, Heath W R. Cross-Presentation: A General Mechanism for C T L Immunity and Tolerance. *Immunology Today* 1998; 19: 368–373.
6. Immunosuppressive Agents. In, *Goodman Gilman's The Pharmacological Basis of Therapeutics.* (Gilman A, Rall T, Nies A, and Taylor P, eds.) Pergamon Press, Inc. New York, 1990, pp. 1270–1276.

What is claimed is:

1. A method of treating recurrent cholestatic hepatitis C in a liver transplant recipient comprising:

administering to a liver transplant recipient a dosage of an effective amount of an anti-IL-2 receptor monoclonal antibody and an effective amount of at least one antiviral compound; and repeating administration of said dosage until liver function tests yield values in a clinically acceptable range, wherein said dosage comprises administering either simultaneously or sequentially said anti-IL-2 receptor monoclonal antibody and said at least one antiviral compound.

* * * * *